United States Patent [19]

Fujikura et al.

[11] 4,411,828
[45] Oct. 25, 1983

[54] FRAGRANT TRICYCLIC CARBOXYLATES

[75] Inventors: Yoshiaki Fujikura, Ichikai; Yoshiaki Inamoto; Naotake Takaishi, both of Utsunomiya; Motoki Nakajima, Miyashiro, all of Japan

[73] Assignee: Kao Corporation, Tokyo, Japan

[21] Appl. No.: 239,896

[22] Filed: Mar. 3, 1981

[30] Foreign Application Priority Data

Mar. 14, 1980 [JP] Japan .................................. 55-32434
Dec. 10, 1980 [JP] Japan ................................ 55-174247

[51] Int. Cl.³ ..................... C07C 69/753; A61K 7/46; C11B 9/00
[52] U.S. Cl. ................... 252/522 R; 560/117
[58] Field of Search .......................... 560/117; 252/522

[56] References Cited

U.S. PATENT DOCUMENTS

| | | | |
|---|---|---|---|
| 4,123,394 | 10/1978 | Skorianetz et al. | 252/522 R |
| 4,169,953 | 10/1979 | Aigami | 560/117 |
| 4,275,251 | 6/1981 | Sprecker | 568/817 |
| 4,289,660 | 9/1981 | Schaper | 252/522 |

FOREIGN PATENT DOCUMENTS 2000122 1/1979 United Kingdom ................ 560/117

OTHER PUBLICATIONS

Koch et al., Ann. 638, 111 (1960).
Fieser et al., Reagents for Organic Synthesis, vol. 4 p. 189 (1974).
Weygand, Preparative Organic Chemistry, pp. 368–369, 373–374 (1972).
Survey of Organic Synthesis, N.Y. 1970, p. 818, No. 11.

Primary Examiner—Robert Gerstl
Attorney, Agent, or Firm—Birch, Stewart, Kolasch & Birch

[57] ABSTRACT

Tricyclic carboxylic acid esters having the formula:

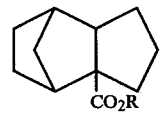

wherein R is an alkyl group of 2 or 3 carbon atoms. These compounds have a woody fragrance and are useful as components of perfume compositions.

2 Claims, No Drawings

FRAGRANT TRICYCLIC CARBOXYLATES

BACKGROUND OF THE INVENTION

The present invention relates to new tricyclic carboxylic acid esters, perfume compositions containing these compounds and methods of preparing the same.

The present inventors have been interested in the fact that, among the terpene compounds, many of those having polycyclic structures have excellent fragrances. The inventors have synthesized numerous compounds having polycyclic structures and have examined the fragrances thereof.

SUMMARY OF THE INVENTION

A primary object of the present invention is to provide novel compounds useful as an ingredient of perfume compositions.

Another object of the present invention is to provide a perfume composition which is stable for a long period of time, even under severe conditions.

Another object of the present invention is to provide methods for producing novel compounds useful as an ingredient of perfume compositions.

These and other objects and advantages of the present invention may be accomplished by the compounds of the following formula (I). Thus, in accordance with the present invention, it has been found that tricyclo[5.5.1.0$^{2.6}$]decane-2-carboxylic acid esters of the following formula (I) have excellent fragrances and high thermal stabilities and quite high stabilities to acidic or alkaline conditions and that they do not become colored or denatured over a long period of time.

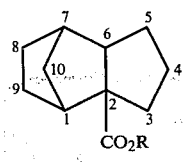

wherein R represents an alkyl radical of 2-3 carbon atoms.

DESCRIPTION OF THE PREFERRED EMBODIMENTS

The fragrance of tricyclic carboxylates of the formula (I) may be classified roughly as a woody fragrance.

The compounds of formula (I) have two isomers as shown by formulae (I-x) and (I-n):

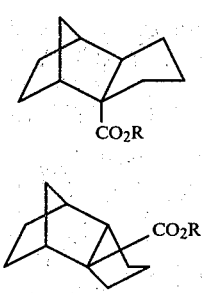

wherein R has the same meaning as defined above.

Isomers of formula (I-x) (exo-trimethylene compounds) have fragrances that are slightly different from isomers of formula (I-n) (endo-trimethylene compounds). More particularly, the former compounds have a lemon-like (citrus-fruity-woody) odor and the latter compounds have a fresh-woody-earthy odor.

The compound of formula (I) wherein R represents a methyl group has been known as an interesting compound in synthetic chemistry (H. Koch and W. Haaf, Ann. 638, 111 (1960)) or as an intermediate for the production of antiviral agents (Japanese Laid Open Patent Application No. 53-82765 (1978)). The present inventors found that these methyl esters have a herbal fragrance and have filed a patent application directed to this concept (Japanese Patent Application Serial No. 55-32435).

It has now been found unexpectedly that if the alkyl group is varied, the flavor of the ester is also varied. The present invention has been completed on the basis of this finding.

As the alkyl group R in the above formula (I), there may be mentioned ethyl, n-propyl and i-propyl groups. Among them, the compound of the ethyl ester exhibits the strongest odor.

Tricyclic carboxylic acid esters of formula (I) of the present invention have the above-described, specific odors and excellent properties such as a high thermal stability and a high stability to both acidic and alkaline conditions and they do not become colored or denatured over a long period of time. Generally, when perfumes are incorporated in acidic or alkaline detergents, they are exposed to severe conditions such as pH 1-4 or pH 10-13, respectively, and as the temperature is elevated, their smells often are altered or degraded. However, the tricyclic carboxylic acid esters of the present invention are stable and free of such phenomena.

As a matter of course, the tricyclic carboxylic acid esters of the present invention may be incorporated in products in which perfume materials are generally used, such as perfumes, soaps, shampoos, hair rinses, detergents, cosmetics, floor waxes, sprays and aromatics, in addition to the acidic and alkaline detergents.

Structurally, the tricyclic carboxylic acid esters of the present invention are esterification products of the acids (II) with an alcohol ROH wherein R has the same meaning as defined above. However, it has been found that the reaction hardly proceeds when the free acid is directly esterified with the alcohol. It is advantageous that free acid (II) be first converted into acid halide (III) and then acid halide (III) reacted with an alcohol to form ester (I).

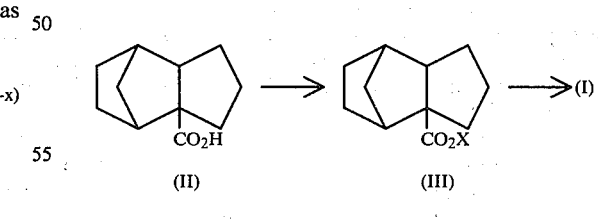

wherein X represents Cl or Br.

Acid halide (III) may be obtained by reacting free acid (II) with a halogenating agent such as thionyl chloride, phosphorus trichloride, phosphorus pentachloride, thionyl bromide, phosphorus tribromide or phosphorus pentabromide by an ordinary process. For obtaining ester (I), the acid halide (III) thus formed is reacted with an alcohol ROH. The reaction proceeds generally at room temperature without any heating. The alcohol ROH includes ethyl alcohol, n-propyl alcohol and i-propyl alcohol. The alcohol is suitably used in an excess amount relative to acid halide (III). The intended product (I) is obtained nearly quantitatively.

Another process wherein free acid (II) is reacted with an esterifying agent such as a dialkyl sulfate to form ester (I) may be employed in place of the above process wherein the ester is formed via the acid halide.

Dialkyl sulfates having alkyl groups of 2 to 3 carbon atoms may be used in the present invention. Examples thereof include diethyl sulfate, di-n-propyl sulfate and di-i-propyl sulfate. Any lower alcohols, for example, methanol, ethanol and i-propanol, may be used as the reaction medium to form esters with a dialkyl sulfate. In this process, no alkaline or acid catalyst is needed.

The present inventors have further found that if the carboxylic acid (II) is reacted with a dialkyl sulfate in the presence of an aqueous alkali solution without using any organic solvent such as acetone or lower alcohols, the ester (I) can be obtained in a high yield without any difficulty in stirring the reaction system during the reaction. In addition, the after-treatment can be effected easily because of the absence of an organic solvent and the fact that by-products are formed in only an extremely small amount.

As the aqueous alkali solution used in the above process, there may be mentioned alkali metal hydroxides and alkali metal carbonates in an aqueous solution. As the alkali metals, sodium and potassium are most suitable. The aqueous alkali solution may be a 5–50% solution of the above alkali substance, preferably a 10–30% solution thereof. The dialkyl sulfate may be used in an amount of 1.0–2.0 moles, particularly about 1.0–1.4 moles, per mole of the carboxylic acid (II). The alkali substance may be used in an amount of at least 1 mole, suitably 1.0–1.5 moles and most preferably about 1.0–1.2 moles, per mole of the carboxylic acid.

The reaction is preferably carried out by adding an aqueous alkali solution dropwise to a solution of a mixture of carboxylic acid (II) and the dialkyl sulfate. It has been found that the yield of the carboxylic acid ester can be increased by adding the aqueous alkali solution in at least two portions and that after the addition of a portion thereof, allowing the mixture to react for a proper period of time and then taking out the aqueous layer, this operation being repeated at least two times. A reason therefor is considered to be as follows. Water in the reaction system plays a role of dissolving the alkali substance and the alkali metal salt of monoalkyl sulfate formed. Further, the water inhibits the improvement in yield of the product, since it decomposes the reactant dialkyl sulfate. If the water is properly removed from the reaction system, the decomposition of dialkyl sulfate can be prevented. The number of times of addition of the portions of aqueous alkali solution is suitably up to about 10, since if the number of times of addition is excessive, the operation becomes too complicated, though the yield is improved as the number is increased. Alternatively, the aqueous alkali solution may be added not in portions but dropwise continuously and only the aqueous layer is taken out continuously. For example, if the aqueous alkali solution is added at once in the case that 1.1 moles of diethyl sulfate and 1.1 moles of sodium hydroxide are used per mole of the carboxylic acid (II) as shown in the following example, the per-pass yield (after the purification) of the ethyl carboxylate is 81%, whereas in case the aqueous alkali solution is added in two portions, the pre-pass yield is 90% and in case said solution is added in four portions the per-pass yield is 93%.

The free acid (II) used as the starting material is obtained by (A) a process wherein water is added to dicyclopentadiene (VI) in the presence of an acid catalyst to form a hydrate followed by hydrogenation and then the hydrate is subjected to a Koch carboxylation reaction or (B) a process wherein one of the two unsaturated bonds is hydrogenated and then it is subjected to the Koch carboxylation reaction:

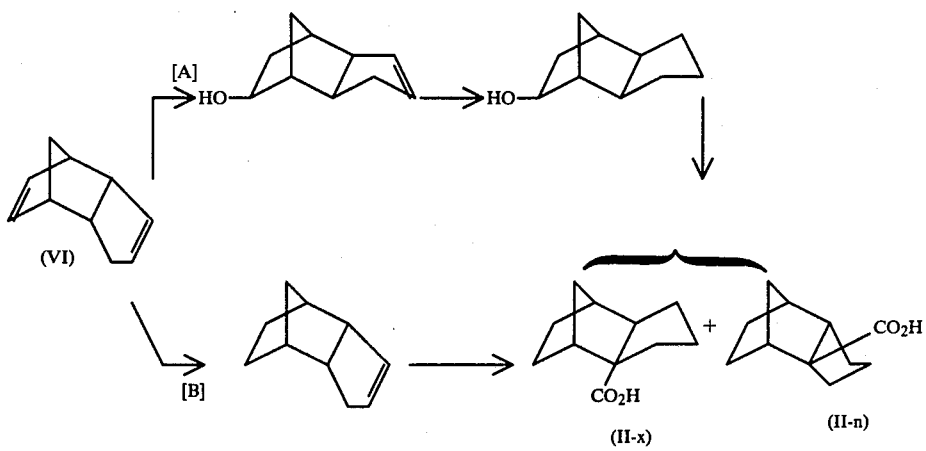

By either process (A) or (B), the resulting free acid is a mixture of exo-trimethylene compound (II-x) and endo-trimethylene compound (II-n). The ratio of (II-x) to (II-n) is generally 1:1, but it varies depending on the conditions.

The free acid mixture may be esterified directly by the above described process without the separation of the mixture into the respective components, thereby forming the ester which may directly be used as a perfume material.

In case either the exo-trimethylene ester (I-x) or endo-trimethylene ester (I-n) is to be obtained alone or a mixture thereof containing either (I-x) or (I-n) in a larger amount, the following process (1) or (2) may be employed: (1) a process wherein the mixture of the esters is divided into the respective components precisely by distillation, and (2) a process wherein the mixture of free acids is converted to their methyl esters, which are then divided into the respective components precisely by distillation, and wherein one of the intended components is hydrolyzed into the free acid again and the free acid is converted to its intended ester (II). Process (1) is industrially advantageous. Process (2) is advantageous when either ester (I-x) or (I-n) is to be obtained in a high purity, since the isolated free acid (II-x) or (II-n) can be recrystallized.

The following examples further illustrate the present invention, which by no means should be regarded as a limitation of the present invention.

EXAMPLE 1

30 ml. of ethanol was added dropwise to 30 g (151 millimoles) of exo-tricyclo [$5.2.1.0^{2,6}$]decane-endo-2-carboxylic acid chloride (exo-trimethylene compound of formula (III) wherein X represents Cl) which had been synthesized by the process of Koch et al as described above under stirring and under external cooling with ice. After completion of the addition, the mixture was stirred at room temperature for 2 hours and then excessive ethanol was distilled out. 100 ml. of ethyl ether was added thereto and the resulting ether layer was washed thoroughly with a saturated aqueous solution of sodium hydrogen carbonate. Then, it was washed with a saturated aqueous solution of common salt. The organic layer was dried with anhydrous magnesium sulfate and filtered. The solvent was distilled out to obtain 30.2 g (yield 96%) of crude ethyl exo-tricyclo [$5.2.1.0^{2,6}$]decane-endo-2-carboxylate (I-x, R=ethyl). This product was distilled under reduced pressure (136 C/21 mmHg) to obtain the pure product. The product had a citrus-fruity-woody odor and was an excellent perfume material.

Elementary analysis as $C_{13}H_{20}O_2$: Theoretical (%): C, 74.96; H, 9.68: Found (%): C, 74.75; H, 9.58.

IR (neat): 1730, 1300, 1170, 1080 cm$^{-1}$ $^1$HNMR (CCl$_4$ solvent, TMS internal standard, $\delta$), 4.07 (quartet, J=7 Hz, —OCH$_2$—), 2.57–0.73 (complicated multiplet), 1.07 (triplet, J=7 Hz, —CH$_2$CH$_3$)

MS (Relative strength): 208 (M+, 12), 162 (57), 141 (100), 135 (60), 134 (52), 113 (61), 95 (32), 80 (35), 67 (82), 41 (38)

EXAMPLE 2

The reaction was carried out under the same conditions as in Example 1 except that ethanol was replaced with n-propyl alcohol. n-Propyl exo-tricyclo[$5.2.1.0^{2,6}$]-decane-endo-2-carboxylate (I-x, R=n-propyl) was obtained in a yield of 95%.

Elementary analysis as $C_{14}H_{22}O_2$: Theoretical (%): C, 75.63; H, 9.97: Found (%): C, 75.51; H, 9.80.

IR (neat): 1730, 1270, 1240, 1170 cm$^{-1}$ $^1$HNMR (CCl$_4$ solvent, TMS internal standard, $\delta$) 3.9 (triplet, J=7 Hz, —OCH$_2$—), 2.5–0.8 (complicated multiplet)

MS (Relative strength): 222 (M+, 7), 162 (42), 155 (39), 135 (66), 134 (46), 113 (99), 79 (32), 67 (100), 43 (36), 41 (66)

EXAMPLE 3

The reaction was carried out under the same conditions as in Example 1 except that ethanol was replaced with i-propyl alcohol. i-Propyl-exo-tricyclo[$5.2.1.0^{2,6}$]-decane-endo-2-carboxylate (I-x, R=i propyl) was obtained in a yield of 94%.

Boiling point: 50 C/0.03 mmHg

Elementary analysis as $C_{14}H_{22}O_2$: Theoretical (%): C, 75.63; H, 9.97: Found (%): C, 75.61; H, 9.64.

IR (neat): 1720, 1300, 1270, 1240, 1170, 1110 cm$^{-1}$ $^1$HNMR (CCl$_4$ solvent, TMS internal standard, $\delta$) 4.9 (heptaplet, J=6 Hz, —OCH<), 2.5–0.9 (complicated multiplet), 1.2 (doublet, J=6 Hz)

MS (Relative strength): 222 (M+, 4), 135 (58), 134 (24), 113 (89), 93 (29), 80 (27), 79 (28), 67 (100), 43 (44), 41 (59)

EXAMPLE 4

Endo-tricyclo[$5.2.1.0^{2,6}$]decane-exo-2-carboxylic acid (II-n) synthesized by the above described process of Koch et al was reacted with thionyl chloride according to the process of Koch et al to obtain an acid chloride (endo-trimethylene of formula (III) wherein X=Cl) (b.p. 140 C/20 mmHg). 30 g (151 millimoles) of the acid chloride was charged in a reaction vessel and then 30 ml of ethyl alcohol was added thereto dropwise under stirring and under external cooling with ice. After completion of the addition, the mixture was stirred at room temperature for 2 hours and then excessive ethyl alcohol was distilled out. 110 ml. of ethyl ether was added thereto and the resulting ether layer was washed thoroughly with a saturated aqueous solution of sodium hydrogen carbonate. Further, it was washed with a saturated aqueous solution of common salt. The ether layer was dried with anhydrous magnesium sulfate and filtered. The solvent was distilled out to obtain 30.7 g (yield 98%) of crude ethyl endo-tricyclo[$5.2.1.0^{2,6}$]decane-exo-2-carboxylate. This crude product was distilled under reduced pressure (141 C/19 mmHg) to obtain the pure ester. The product had a fresh woody-earthy odor and was excellent as a perfume component.

Elementary analysis as $C_{13}H_{20}O_2$: Theoretical (%): C, 74.96; H, 9.68: Found (%): C, 75.10; H, 9.59.

IR (neat): 1730, 1270, 1230, 1220, 1170, 1160 cm$^{-1}$ $^1$HNMR (CCl$_4$ solvent, TMS internal standard, $\delta$), 4.80 (quartet, J=7 Hz, —OCH$_2$—), 3.08–1.33 (complicated multiplet), 1.21 (triplet, J=7 Hz, —CH$_2$CH$_3$)

MS (Relative strength: 208 (M+, 6), 141 (39), 136 (12), 135 (100), 134 (15), 113 (14), 93 (17), 79 (16), 67 (46), 41 (15)

EXAMPLE 5

The reaction was carried out under the same conditions as in Example 4 except that ethanol was replaced with n-propyl alcohol. n-Propyl endo-tricyclo[$5.2.1.0^{2,6}$]decane-exo-2-carboxylate was obtained in a yield of 95%.

Boiling point: 64° C./0.02 mmHg

Elementary analysis as $C_{14}H_{22}O_2$: Theoretical (%): C, 75.63; H, 9.97: Found (%): C, 75.41; H, 9.85.

IR (neat): 1730,1270,1240,1220,1170,1160 cm$^{-1}$ $^1$NHMR (CCl$_4$ solvent, TMS internal standard,$\delta$) 3.9 (triplet, J=6 Hz, —OCH$_2$CH$_2$—), 3.0–1.1 (complicated multiplet), 0.9 (triplet, J=7 Hz, —CH$_3$)

MS (Relative strength): 222(M+, 3), 155 (21), 135 (100), 134 (15), 113 (27), 93 (19), 79(19), 67(61), 43(15), 41(31).

EXAMPLE 6

The reaction was carried out under the same conditions as in Example 4 except that ethanol is replaced with i-propyl alcohol. i-Propyl endo-tricyclo[$5.2.1.0^{2,6}$]-decane-exo-2-carboxylate was obtained.

Boiling point: 52° C./0.02 mmHg

Elementary analysis as $C_{14}H_{22}O_2$: Theoretical (%): C, 75.63; H, 9.97: Found (%): C, 75.42; H, 9.85.

IR (neat): 1725,1270,1240,1220,1170,1110 cm$^{-1}$ $^1$HNMR (CCl$_4$ solvent, TMS internal standard, δ) 4.85 (heptaplet, J=6 Hz, —OCH<), 2.9–1.3 (complicated multiplet), 1.15 (doublet, J=6 Hz, —CH$_3$).

MS (relative strength) 222(M+,3), 155(15), 135(100), 134(15), 113(38), 93(19), 79(17), 67(55), 43(17), 41(23).

EXAMPLE 7

A tricyclo[5.2.1.0$^{2,6}$]decane-2-carboxylic acid mixture (II-x/II-n=3/2) synthesized by the above described synthesis method of H. Koch et al was reacted with thionyl chloride according to the process of Koch et al to obtain an acid chloride. 300 g (1.51 mole) of the acid chloride mixture was reacted with 300 ml. of ethyl alcohol in the same manner as in Example 1 to obtain 302 g (yield 96%) of crude ethyl tricyclo[5.2.1.0$^{2,6}$]decane-2-carboxylate (I-x and I-n, R=Et). This crude product was subjected to fractional distillation in a precision distillation device (theoretical number of stages: 50) under reduced pressure (10 mmHg) to obtain 22 g of an initial fraction, 129 g of ethyl exo-tricyclo[5.2.1.0$^{2,6}$]decane-endo-2-carboxylate (I-x, R=Et), 34 g of an intermediate fraction, 83 g of ethyl endo-tricyclo [5.2.1.0$^{2,6}$]decane-exo-2-carboxylate (I-x, R=Et) and 34 g of a residue. The residue mainly comprised endo-tricyclo[5.2.1.0$^{2,6}$]decane-exo-2-carboxylic acid according to gas chromatographic analysis.

EXAMPLE 8

A floral fragrance composition for detergents was prepared with the following composition:

| | |
|---|---|
| β-Phenethyl alcohol | 200 |
| p-t-Butyl-α-methylhydrocinnamic aldehyde | 40 |
| Linalool | 50 |
| γ-Methylionone | 40 |
| Menthanylacetate | 20 |
| α-Hexylcinnamic aldehyde | 200 |
| Benzyl salicylate | 40 |
| Styraryl acetate | 20 |
| Terpineol | 40 |
| Patchouli oil | 10 |
| Geranium oil | 20 |
| Cedryl acetate | 50 |
| Benzyl acetate | 60 |
| Musk ambrette | 20 |
| Musk Ketone | 20 |
| Coumarin | 20 |
| Geraniol | 50 |
| | 900 |

100 g of ethyl endo-tricyclo[5.2.1.0$^{2,6}$]decane-exo-2-carboxylate was added to 900 g of the above fragrance composition to obtain a mixed fragrance composition having a slightly green fragrance with a woody note.

EXAMPLE 9

A herbal fragrance composition for shampoos having the following composition was prepared:

| | |
|---|---|
| Terpinyl acetate | 130 |
| Cedarwood virginia | 100 |
| Bergamot oil | 155 |
| Oak moss absolute | 60 |
| Amyl salicylate | 60 |
| Coumarin | 60 |
| Galibanum resinoide | 40 |
| Musk ketone | 20 |
| Cedryl acetate | 40 |
| Citronellol | 40 |
| Geraniol | 40 |
| Lavandin oil | 40 |
| Eugenol | 10 |
| Geranyl acetate | 20 |
| Geranium oil | 30 |
| Patchouli oil | 25 |
| Neroli oil | 30 |
| | 900 |

100 g of propyl endo-tricyclo[5.2.1.0$^{2,6}$]decane-exo-2-carboxylate was added to 900 g of the above fragrance composition to obtain a mixed fragrance composition having a floral fragrance with a woody scent.

EXAMPLE 10

A floral fragrance composition for detergents was prepared with the following composition:

| | |
|---|---|
| Aldehyde C-12 | 2 |
| Benzoin resinoid | 5 |
| Cinnamic alcohol | 100 |
| Citronellol | 100 |
| Cyclamen aldehyde | 20 |
| Decenal | 1 |
| Jasmine base | 200 |
| Linalool | 130 |
| γ-Methylionone | 40 |
| p-T.B.C.H.A. (p-tert-butylcyclohexyl acetate) | 70 |
| β-Phenethyl alcohol | 140 |
| Tetralin musk | 50 |
| Dimethylbenzylcarbinyl acetate | 42 |
| | 900 |

100 g of ethyl exo-tricyclo[5.2.1.0$^{2,6}$]decane-endo-2-carboxylate was added to 900 g of the above fragrance composition to obtain a novel mixed fragrance composition having a fruity, sweet odor with a woody note.

EXAMPLE 11

A fougére fragrance composition for shampoos was prepared with the following composition:

| | |
|---|---|
| Coumarin | 20 |
| Acetylcedrene | 35 |
| Benzyl benzoate | 55 |
| α-Ionone | 50 |
| Lavandin concrete | 55 |
| Oak moss absolute | 50 |
| Musk ambrette | 55 |
| Benzoin resinoid | 50 |
| Amyl salicylate | 85 |
| Lavandin oil | 100 |
| Cedarwood oil | 100 |
| Rose base | 245 |
| | 900 |

100 g of isopropyl exo-tricyclo[5.2.1.0$^{2,6}$]decane-endo-2-carboxylate was added to 900 g of the above fragrance composition to obtain a novel mixed fragrance composition having a fresh odor with a woody note.

EXAMPLE 12

0.1% of ethyl tricyclo[5.2.1.0$^{2,6}$]decane-2-carboxylate (mixture of exo-trimethylene ester and endo-trimethylene ester in a ratio of approximately 1:1) was added to an acidic detergent of pH 1.5 and an alkaline detergent of pH 10.9. After storage for 20 days, changes in odor were examined to obtain the results shown in the following table:

| | Odor Stability | | | |
|---|---|---|---|---|
| | −5 °C. | 30 °C. | 40 °C. | 50 °C. |
| Fragrance of the present invention | Acidic detergent (pH 1.5) | o | o | o | o |
| | Alkaline detergent (pH 10.9) | o | o | o | o |
| A generally used fragrance | Acidic detergent (pH 1.5) | o | Δ | x | x |
| | Alkaline detergent (pH 10.9) | o | o | Δ | Δ |

Functional judgment:
o: Stable, no change.
Δ: Some change, The original odor still remains.
x: Unstable, Serious change. The original odor does not remain.

EXAMPLE 13

1.8 g (10 millimoles) of endo-tricyclo[5.2.1.0$^{2,6}$]decane-exo-2-carboxylic acid (II-n) was dissolved in 20 ml. of ethanol. 1.7 g (11 millimoles) of diethyl sulfate was added to the solution and the whole reaction mixture was refluxed for 1.5 hours. Then, ethanol was distilled out. 10 ml. of water was added to the residue and the whole mixture was refluxed for an additional 30 minutes. After allowing the mixture to cool, 10 ml. of ethyl ether was added thereto to effect the fractionation. The ether layer was washed with aqueous common salt solution, dried with anhydrous magnesium sulfate and filtered. The solvent was distilled out to obtain 2.04 g (yield of crude product 98%) of crude ethyl endo-tricyclo[5.2.1.0$^{2,6}$]decane-exo-2-carboxylate (I-n, R=ethyl). The crude product was distilled under reduced pressure (b.p. 141 C/19 mmHg) to obtain 1.65 g (yield 80%) of the pure ester.

EXAMPLE 14

The reaction was carried out under the same conditions as in Example 13 except that the carboxylic acid was replaced with exo-tricyclo[5.2.1.0$^{2,6}$]decane-endo-2-carboxylic acid to obtain ethyl exo-tricyclo[5.2.1.0$^{2,6}$]decane-endo-2-carboxylate (I-x, R=ethyl) in a yield of 98% (crude) and 79% (pure), respectively.

EXAMPLE 15

110 g (0.55 mole) of 20% aqueous sodium hydroxide was added dropwise to a mixture of 90.0 g (0.5 mole) of tricyclo[5.2.1.0$^{2,6}$]decane-2-carboxylic acids (mixture of endo and exo compounds) and 84.8 g (0.55 mole) of diethyl sulfate over 2 hours under stirring at 50 C.°. After completion of the addition, the stirring was continued for 30 minutes. Then, 16.5 g (0.0825 mole) of 20% aqueous sodium hydroxide solution was added thereto and the whole mixture was stirred at 100 C.° for 45 minutes in order to decompose unreacted sulfate. After completion of the decomposition, the mixture was allowed to stand at room temperature for a while to form layers. By means of the distillation, 84.2 g (yield 81%) of pure ethyl tricyclo[5.2.1.0$^{2,6}$]decane-2-carboxylate was obtained. If was revealed by fractional distillation that the product was a mixture of ethyl exo-tricyclo[5.2.1.0$^{2,6}$]decane-endo-2-carboxylate and ethyl endo-tricyclo[5.2.1.0$^{2,6}$]decane-exo-2-carboxylate.

EXAMPLE 16

55.0 g (0.275 mole) of 20% aqueous sodium hydroxide solution was added dropwise to a mixture of 90.0 g (0.5 mole) of tricyclo[5.2.1.0$^{2,6}$]decane-2-carboxylic acid (mixture of endo and exo compounds) and 84.8 g (0.55 mole) of diethyl sulfate over one hour under stirring at 50 C.°. After completion of the addition, the stirring was continued at that temperature for 30 minutes. After completion of the stirring, the mixture was allowed to stand at room temperature for a while to form layers. The lower aqueous layer was taken out. The temperature was elevated again to 50 C.°. 55.0 g (0.275 mole) of a 20% aqueous sodium hydroxide solution was added dropwise to the remainder over one hour under stirring at that temperature for 30 minutes. Then, 16.5 g (0.0825 mole) of 20% aqueous sodium hydroxide solution was added thereto and the whole reaction mixture was stirred at 100 C.° for 45 minutes in order to decompose unreacted diethyl sulfate. The mixture was allowed to cool and divided into layers. After the distillation, 93.6 g (yield 90.0%) of pure ethyl tricyclo[5.2.1.0$^{2,6}$]decane-2-carboxylate was obtained.

EXAMPLE 17

110 g (0.55 mole) of 20% aqueous sodium hydroxide solution was dividedly added dropwise in 4 portions to 90.0 g (0.5 mole) of the same carboxylic acid as used in Example 16 and treated in the same manner as in Example 16 to obtain 96.7 g (yield 93%) of pure ethyl tricyclo[5.2.1.0$^{2,6}$]decane-2-carboxylate.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A perfume composition comprising a tricyclo[5.2.1.0$^{2,6}$]decane-2-carboxylic acid ester of the formula (I):

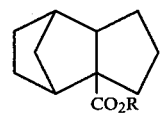

(I)

wherein R is an alkyl group of 2 or 3 carbon atoms, in an amount sufficient to give a woody note thereto.

2. A perfume composition according to claim 1, wherein R is ethyl.

* * * * *